United States Patent
Ochiai et al.

(10) Patent No.: US 10,840,601 B2
(45) Date of Patent: Nov. 17, 2020

(54) HORN ANTENNA ARRAY

(71) Applicant: PIONEER CORPORATION, Tokyo (JP)

(72) Inventors: Takanori Ochiai, Kawagoe (JP);
Hiroyuki Tanaka, Kawagoe (JP);
Tatsuya Kawano, Kawagoe (JP);
Masakazu Ogasawara, Kawagoe (JP)

(73) Assignee: PIONEER CORPORATION, Tokyo (JP)

( * ) Notice: Subject to any disclaimer, the term of this patent is extended or adjusted under 35 U.S.C. 154(b) by 0 days.

(21) Appl. No.: 16/085,329

(22) PCT Filed: Mar. 14, 2016

(86) PCT No.: PCT/JP2016/058015
§ 371 (c)(1),
(2) Date: Sep. 14, 2018

(87) PCT Pub. No.: WO2017/158696
PCT Pub. Date: Sep. 21, 2017

(65) Prior Publication Data
US 2019/0115666 A1    Apr. 18, 2019

(51) Int. Cl.
*H01Q 13/02*    (2006.01)
*H01Q 17/00*    (2006.01)
(Continued)

(52) U.S. Cl.
CPC ............ *H01Q 13/02* (2013.01); *H01Q 17/00* (2013.01); *H01Q 17/001* (2013.01);
(Continued)

(58) Field of Classification Search
CPC ...... H01Q 21/064; H01Q 13/02; H01Q 19/17; H01Q 21/0087; H01Q 13/025;
(Continued)

(56) References Cited

U.S. PATENT DOCUMENTS 2,851,686 A * 9/1958 Hagaman ............... H01Q 13/02
343/786
2,908,002 A * 10/1959 Atta ....................... H01Q 15/14
343/776
(Continued)

FOREIGN PATENT DOCUMENTS

JP    H07-297622 A    11/1995
JP    2010-062994 A    3/2010

OTHER PUBLICATIONS

International Search Report for related International Application No. PCT/JP2016/058015, dated Apr. 12, 2016; 1 page.

*Primary Examiner* — Hai V Tran
(74) *Attorney, Agent, or Firm* — Procopio, Cory, Hargreaves & Savitch LLP (57) ABSTRACT

A horn antenna array is provided with a plurality of horn antennas arranged in one direction. Each of the plurality of horn antennas includes two pairs of inclined planes, which define a frustum-shape horn, and on an electromagnetic wave incident side of the horn, ends of a pair of inclined planes arranged in the one direction out of the two pairs of inclined planes project from ends of the other pair of inclined planes out of the two pairs of inclined planes.

7 Claims, 5 Drawing Sheets

(51) Int. Cl.
   *H01Q 21/00*   (2006.01)
   *H01Q 21/08*   (2006.01)
   *H01Q 21/06*   (2006.01)

(52) U.S. Cl.
   CPC ......... *H01Q 21/00* (2013.01); *H01Q 21/0031* (2013.01); *H01Q 21/064* (2013.01); *H01Q 21/08* (2013.01); *A61M 2230/65* (2013.01)

(58) Field of Classification Search
   CPC .. H01Q 13/0208; H01Q 17/001; H01Q 17/00; H01Q 21/0031; H01Q 21/00; H01Q 21/08
   USPC .................................. 343/778, 776, 854, 786
   See application file for complete search history.

(56) References Cited

U.S. PATENT DOCUMENTS

| | | | |
|---|---|---|---|
| 4,087,822 A | | 5/1978 | Maybell et al. |
| 4,185,286 A | * | 1/1980 | Drabowitch ......... H01Q 3/2658 343/754 |
| 5,898,409 A | * | 4/1999 | Holzman ............... H01Q 13/02 333/25 |
| 6,441,795 B1 | * | 8/2002 | Volman ................. H01Q 13/02 343/786 |
| 2005/0231436 A1 | * | 10/2005 | McLean ............... H01Q 3/0275 343/786 |
| 2009/0184881 A1 | * | 7/2009 | Bullock ................. H01Q 1/288 343/873 |
| 2010/0060537 A1 | * | 3/2010 | Nagayama ............ H01Q 1/247 343/776 |
| 2010/0097283 A1 | * | 4/2010 | Hino ...................... H01Q 9/285 343/786 |
| 2015/0029065 A1 | * | 1/2015 | Cheng ................... H01Q 19/06 343/753 |

* cited by examiner

HORN ANTENNA ARRAY

CROSS-REFERENCE TO RELATED APPLICATIONS

This application is a U.S. National Stage entry of PCT Application No: PCT/JP2016/058015 filed Mar. 14, 2016, the contents of which are incorporated herein by reference.

TECHNICAL FIELD

The present invention relates to a horn antenna array used to measure an electromagnetic wave, such as, for example, a terahertz wave.

BACKGROUND ART

For this type of antenna array, for example, there is proposed an antenna array in which a plurality of horns that communicate with a waveguide are formed (refer to Patent Literature 1).

CITATION LIST

Patent Literature

Patent Literature 1: Japanese Patent Application Laid Open No. 2010-62994

SUMMARY OF INVENTION

Technical Problem

In a design stage of the apparatus, it is assumed in many cases that an electromagnetic wave to be measured enters perpendicularly to a detector(s). In reality, however, the electromagnetic wave to be measured may enter obliquely to the detector(s) in some cases, for example, due to diffused reflection on a surface of a measurement target, an arrangement error of the detectors, or the like. In order to detect the electromagnetic wave that enters obliquely, there is a possible method of expanding an opening of a horn; however, resolution may be deteriorated due to a reduction in density of the detectors.

In view of the aforementioned problem, it is therefore an object of the present invention to provide a horn antenna array that is configured to efficiently detect the electromagnetic wave that enters obliquely, while preventing the deterioration in the resolution.

Solution to Problem

The above object of the present invention can be achieved by a horn antenna array provided with a plurality of horn antennas arranged in one direction, wherein each of the plurality of horn antennas includes two pairs of inclined planes, which define a frustum-shape horn, and on an electromagnetic wave incident side of the horn, ends of a pair of inclined planes arranged in the one direction out of the two pairs of inclined planes project from ends of the other pair of inclined planes out of the two pairs of inclined planes.

The operation and other advantages of the present invention will be clarified from Description of Embodiments explained below.

BRIEF DESCRIPTION OF DRAWINGS

FIG. 2A is a front view, FIG. 2B is a side view.

FIG. 6A is a front view, FIG. 6B is a side view.

FIG. 7 is a perspective view illustrating a horn antenna array according to a second example.

DESCRIPTION OF EMBODIMENTS

A horn antenna array according to embodiments of the present invention will be explained.

A horn antenna array according to an embodiment is provided with a plurality of horn antennas arranged in one direction. Each of the plurality of horn antennas includes two pairs of inclined planes, which define a frustum-shape horn. On an electromagnetic wave incident side of the horn, ends of a pair of inclined planes arranged in the one direction out of the two pairs of inclined planes project from ends of the other pair of inclined planes out of the two pairs of inclined planes.

The "inclined plane" means a plane that is inclined to an incident direction of an electromagnetic wave that enters perpendicularly to a detector of the horn antenna. The "pair of inclined planes arranged in the one direction" means a pair of inclined planes that is parallel to or that is regarded as being substantially parallel to an axis extending in the one direction.

According to studies by the present inventors, the following matter has been found; namely, as a parameter for defining detection characteristics of the horn antenna, for example, there are an opening size of the horn (i.e., a size of the horn on the electromagnetic wave incident side) and a length of the horn.

If the length of the horn is constant, in order to efficiently detect an electromagnetic wave that enters obliquely, the opening size of the horn may be increased. After a certain degree of the opening size of the horn, however, detection efficiency of an electromagnetic wave that enters perpendicularly to the detectors of the horn antennas may be reduced. In addition, it is hard to densely arrange the detectors of the horn antennas due to the opening size of the horn antenna, and resolution associated with the horn antenna array may be deteriorated.

If the opening size of the horn is constant, in order to efficiently detect the electromagnetic wave that enters obliquely, the length of the horn may be reduced. After a certain degree of the length of the horn, however, the detection efficiency of the electromagnetic wave that enters perpendicularly may be reduced.

Here, changing the opening size of the horn while the length of the horn is set constant has the same meaning as changing an opening angle of the horn.

Therefore, if the opening angle of the horn corresponding to the optimum opening size and the optimum length of the horn is realized so that both the detection efficiency of the electromagnetic wave that enters perpendicularly and the detection efficiency of the electromagnetic wave that enters obliquely can be improved to some extent, even a horn that is smaller to some extent than a horn that has the optimum opening size and the optimum length is expected to obtain the same detection efficiency.

In the horn antenna array according to the embodiment, as described above, on the electromagnetic wave incident side of the horn of each horn antenna, the ends of the pair of inclined planes arranged in the one direction (i.e., an arrangement direction) out of the two pairs of inclined planes project from the ends of the other pair of inclined planes.

In other words, the size (or width) in the one direction of each horn antenna (i.e., a distance between the ends of the other pair of inclined planes) is shorter than the size (or width) in a direction that crosses the one direction of each horn antenna (i.e., a distance between the ends of the pair of inclined planes arranged in the one direction). As a result, it is possible to arrange the horn antennas relatively densely. It is thus possible to prevent the deterioration in the resolution associated with the horn antenna array.

Moreover, a distance in a length direction of the horn of the other pair of inclined planes is shorter than a distance in a length direction of the horn of the pair of inclined planes arranged in the one direction. Thus, even if the distance between the ends of the other pair of inclined planes is shorter than the distance between the ends of the pair of inclined planes arranged in the one direction, an angle made by the other pair of inclined planes (i.e., an opening angle) can be set similar to an angle made by the pair of inclined planes arranged in the one direction. It is thus possible to prevent the reduction in the detection efficiency caused by a relatively short distance between the ends of the other pair of inclined planes.

On the other hand, the distance between the ends of the pair of inclined planes arranged in the one direction can be set to improve to some extent both the detection efficiency of the electromagnetic wave that enters perpendicularly and the detection efficiency of the electromagnetic wave that enters obliquely. It is thus possible to improve the detection efficiency of the electromagnetic wave that enters obliquely, as an entire horn antenna.

As a result, according to the horn antenna array in the embodiment, it is possible to efficiently detect the electromagnetic wave that enters obliquely while preventing the deterioration in the resolution.

In one aspect of the horn antenna array according to the embodiment, an angle made by the pair of inclined planes arranged in the one direction is equal to an angle made by the other pair of inclined planes.

According to this aspect, it is possible to prevent the reduction in the detection efficiency caused by the relatively short distance between the ends of the other pair of inclined planes.

In another aspect of the horn antenna array according to the embodiment, the horn antenna array is further provided with a biconvex cylindrical lens extending in the one direction, and the ends of the pair of inclined planes arranged in the one direction are arranged to be brought into contact with or close to a convex surface of the cylindrical lens.

According to this aspect, it is possible to improve the detection efficiency associated with the horn antenna array.

In this aspect, an angle made by the pair of inclined planes arranged in the one direction may correspond to a converging angle of the cylindrical lens.

By virtue of such a configuration, it is possible to efficiently detect an electromagnetic wave that passes through the cylindrical lens, which is extremely useful in practice. The sentence "the angle made by the pair of inclined planes arranged in the one direction may correspond to the converging angle of the cylindrical lens" conceptually includes not only when the angle made by the pair matches the converging angle, but also when the angle made by the pair is greater or less than the converging angle by a minute angle.

EXAMPLES

Hereinafter, a horn antenna array according to examples of the present invention will be explained with reference to the drawings.

First Example

Firstly, a horn antenna array according to a first example of the present invention will be explained with reference to FIG. 1 to FIG. 6.

(Configuration of Horn Antenna Array)

Figure 1:
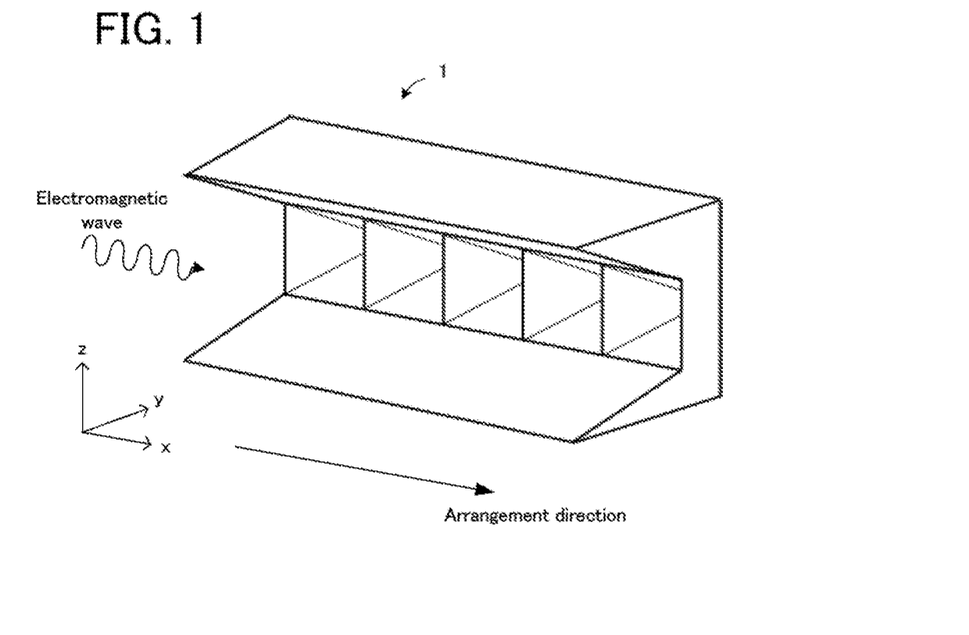
FIG. 1 is a perspective view illustrating a horn antenna array according to a first example.
Figure 2A:
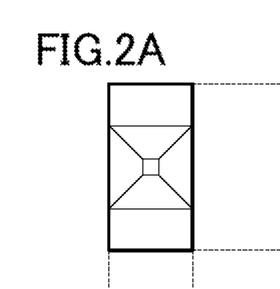
Figure 2B:
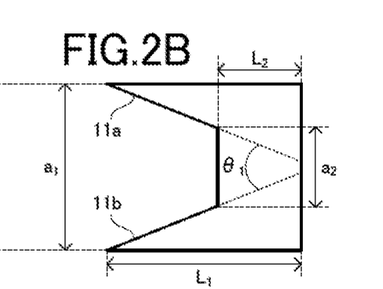
Figure 2C:
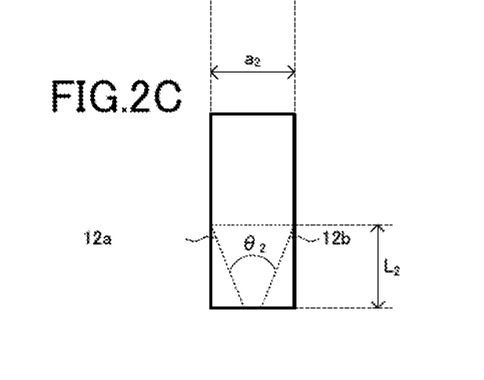
FIG. 2C is a bottom view, illustrating a horn antenna that constitutes the horn antenna array according to the first example.

A configuration of the horn antenna array according to the first example will be explained with reference to FIG. 1 and FIG. 2. FIG. 1 is a perspective view illustrating the horn antenna array according to the first example. FIG. 2 includes a front view (a), a side view (b), and a bottom view (c) illustrating a horn antenna that constitutes the horn antenna array according to the first example.

In FIG. 1, a horn antenna array 1 according to the first example is provided with a plurality of horn antennas arranged in an x-axis direction, which is an example of the "one direction" according to the present invention. Particularly, as illustrated in FIG. 1 and FIG. 2(b), an inner upper surface 11a and an inner lower surface 11b of a horn of the horn antenna array 1 project from ends of an opening of the horn. In other words, the inner upper surface 11a and the inner lower surface 11b of the horn project from inner side surfaces 12a and 12b of the horn, to an electromagnetic wave incident side of the horn antenna array 1.

The "inner upper surface 11a and the inner lower surface 11b" according to the first example and the "inner side surfaces 12a and 12b" are respectively an example of the "pair of inclined planes arranged in the one direction" and the "other pair of title planes" according to the present invention.

Figure 3:
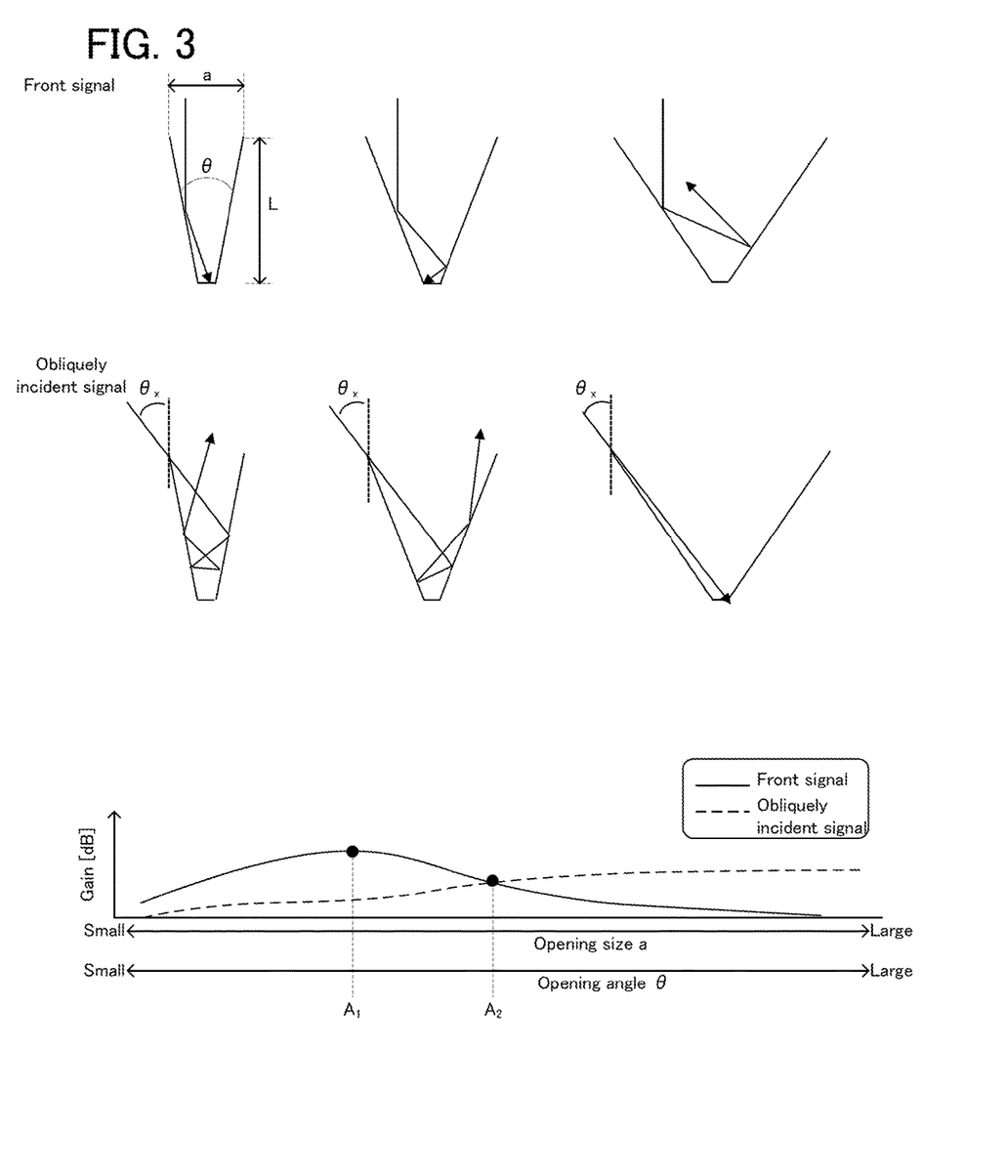
FIG. 3 is a characteristic diagram illustrating an example of a relation between an opening size or an opening angle of the horn antenna and a gain.
Figure 4:
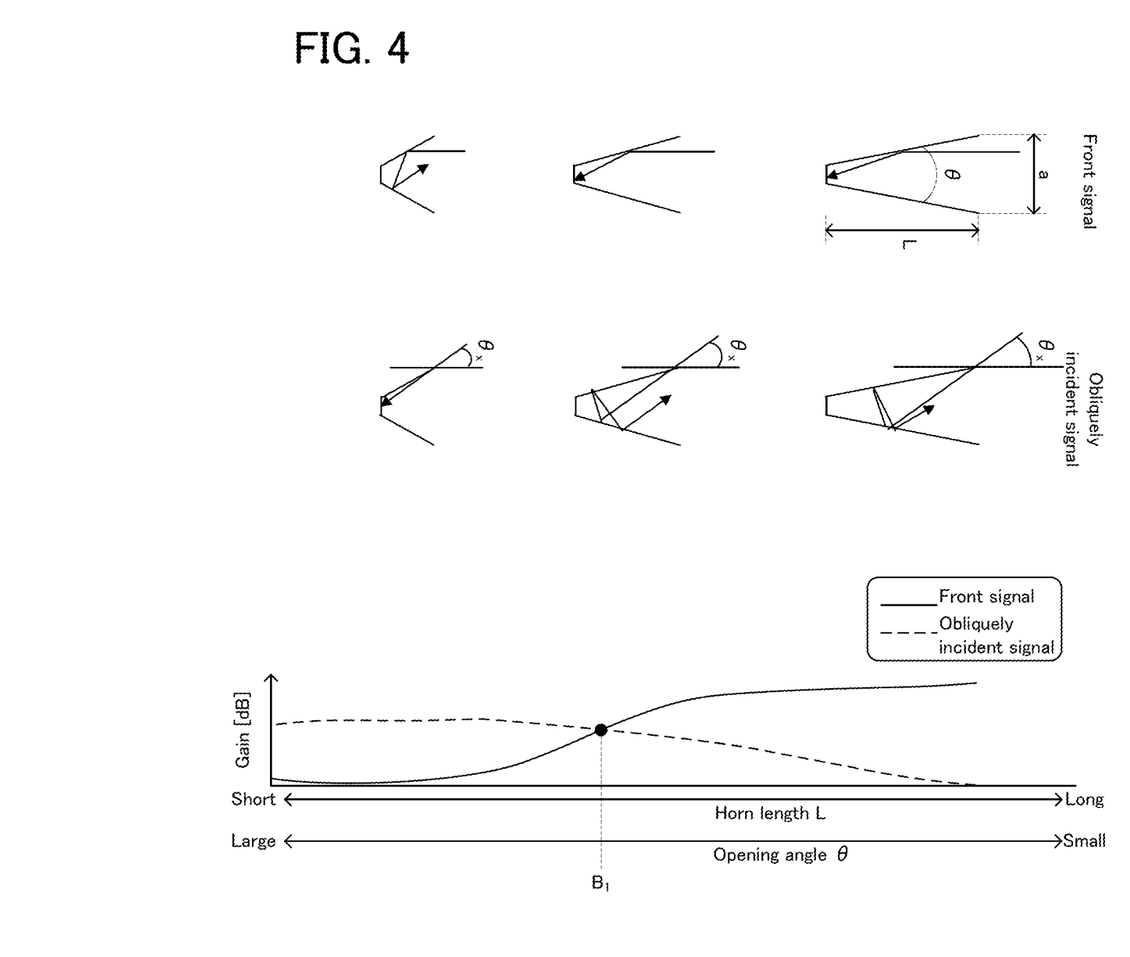
FIG. 4 is a characteristic diagram illustrating an example of a relation between a horn length or the opening angle of the horn antenna and the gain.

Now, characteristics of the horn antenna will be explained with reference to FIG. 3 and FIG. 4. In FIG. 3 and FIG. 4, an electromagnetic wave that enters the horn perpendicularly to a detector of each horn antenna is referred to as a "front signal", and an electromagnetic wave that enters the horn obliquely to the detector is referred to as an "obliquely incident signal".

Firstly, as illustrated in an upper part of FIG. 3, consideration is made on gain (or detection efficiency) associated with a horn antenna when a length L of the horn is set constant and an opening size a of the horn is changed. The opening of the horn is assumed to be a square with a side of a (and the same applies in FIG. 4).

Regarding the front signal, until a certain degree of the opening size a, the front signal easily enters the detector. The gain thus increases in proportion to the opening size a (refer to a solid line in a lower part of FIG. 3). An excessive opening size a, however, may increase the front signal that is reflected by an inner wall of the horn and does not reach the detector, as illustrated in a right end of the "front signal" in the upper part of FIG. 3. The gain thus decreases (refer to the solid line in the lower part of FIG. 3).

On the other hand, regarding the obliquely incident signal, as the opening size a is increased, the gain increases so that the gain asymptotically approaches a certain value (refer to a dashed line in the lower part of FIG. 3).

If only the gain of the front signal is considered, the opening size a may be set to "$A_1$" in the lower part of FIG. 3. If, however, both the gain of the front signal and the gain of the obliquely incident signal are considered, it is desirable to set the opening size a to "$A_2$" in the lower part of FIG. 3. A shape of the dashed line in the lower part of FIG. 3 may change depending on the length L of the horn and an incident angle $\theta_x$ of the obliquely incident signal. Thus, "$A_2$" in the lower part of FIG. 3 may change depending on the length L and the allowed incident angle $\theta$.

Next, as illustrated on a left side of FIG. 4, consideration is made on gain associated with a horn antenna when the opening size a of the horn is set constant and the length L of the horn is changed.

Regarding the front signal, as the length L of the horn is increased, the gain increases so that the gain asymptotically approaches a certain value (refer to a solid line on a right side of FIG. 4). This is because a shorter length L of the horn may increase an opening angle $\theta$ of the horn and may increase the front signal that is reflected by the inner wall of the horn and does not reach the detector.

On the other hand, regarding the obliquely incident signal, as the length L of the horn is reduced, the gain increases so that the gain asymptotically approaches a certain value (refer to a dashed line on the right side of FIG. 4). This is because the shorter length L of the horn may increase the opening angle $\theta$ of the horn.

If only the gain of the front signal is considered, it is desirable to increase the length L of the horn. If, however, both the gain of the front signal and the gain of the obliquely incident signal are considered, it is desirable to set the length L of the horn to "$B_1$" on the right side of FIG. 4. A shape of the dashed line on the right side of FIG. 4 may change depending on the opening size a and the incident angle $\theta_x$. Thus, "$B_1$" on the right side of FIG. 4 may change depending on the opening size a and the incident angle $\theta_x$.

By the way, in studying gain characteristics of each of the front signal and the obliquely incident signal illustrated in FIG. 3 and FIG. 4 from a point of view of the opening angle $\theta$ of the horn, as the opening angle $\theta$ increases, the gain of the front signal decreases and the gain of the obliquely incident signal increases. Moreover, as illustrated in FIG. 4, after a certain degree of the length L of the horn, the gain of the front signal rarely changes.

Based on the above, the present inventors have intended to set the length L of the horn to be long to some extent, and have intended to increase the opening angle $\theta$, thereby to achieve both the gain of the front signal and the gain of the obliquely incident signal.

According to the studies by the present inventors, it has been found that when the length L of the horn is changed while the opening size a of the horn is constant, if the length L of the horn is longer than six times a wavelength $\lambda$ of the electromagnetic wave that is a measurement target, the gain of the front signal is substantially maximal.

It is thus possible to realize both the gain of the front signal and the gain of the obliquely incident signal, by setting $6\lambda$ as the length L of the horn and by obtaining the opening size a corresponding to "$A_2$" in FIG. 3.

Back in FIG. 2, a size of the horn antenna array 1 designed from the aforementioned idea will be specifically explained. In the first example, the wavelength $\lambda$ of the electromagnetic wave that is the measurement target is set to 1 mm (millimeter). In other words, the electromagnetic wave according to the first example is a so-called terahertz wave.

In FIG. 2, a length $L_2$ is 6 mm (i.e., $6\lambda$). An opening size $a_2$ is 5.8 mm. At this time, an angle made by the inner side surfaces 12a and 12b of the horn (i.e., an opening angle $\theta_2$) is 43.6 degrees.

As illustrated in FIG. 1, the plurality of horn antennas are arranged in the x-axis direction in the horn antenna array 1. Thus, in order to prevent the deterioration in resolution associated with the horn antenna array 1 while improving the gain of the obliquely incident signal, a distance in the x-axis direction of each horn antenna (i.e., corresponding to the opening size $a_2$) may be set as short as possible.

On the other hand, a distance in a z-axis direction of each horn antenna can be set long to some extent because it does not influence the resolution. As illustrated in the lower part of FIG. 3, a large opening size a of the horn may improve the gain of the obliquely incident signal.

Thus, in the first example, an opening size $a_1$ in FIG. 2 is set to 11.8 mm and a length $L_1$ is set to 14.8 mm. At this time, an angle made by the inner upper surface 11a and the inner lower surface 11b of the horn (i.e., an opening angle $\theta_1$) is 43.6 degrees.

The size of the horn antenna array 1 described above is an example, and is not limited to this example. The opening angles $\theta_1$ and $\theta_2$ may be different from each other.

Technical Effect

Figure 5:
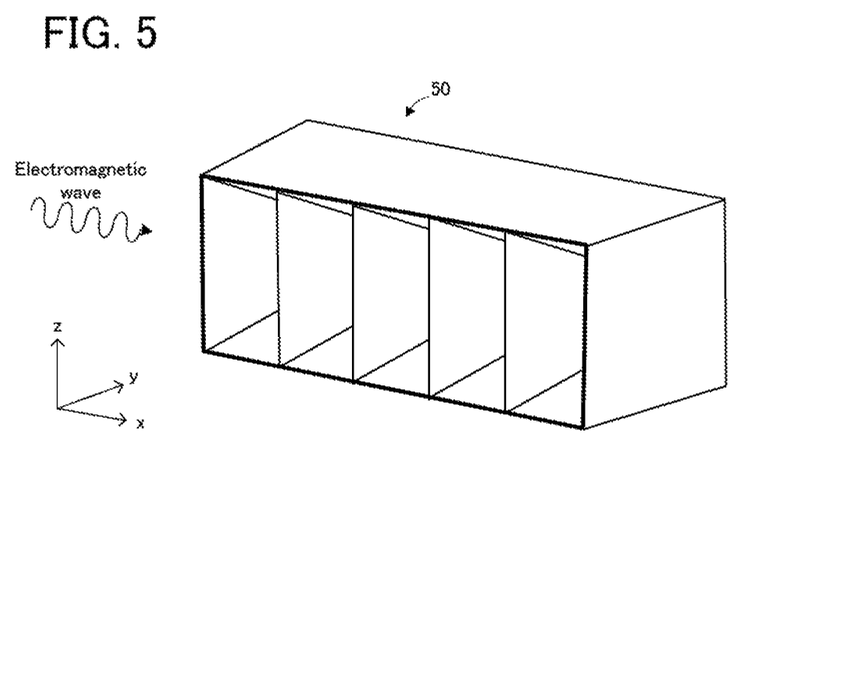
FIG. 5 is a perspective view illustrating a horn antenna array according to a comparative example.
Figure 6A:
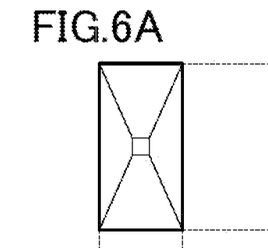
Figure 6B:
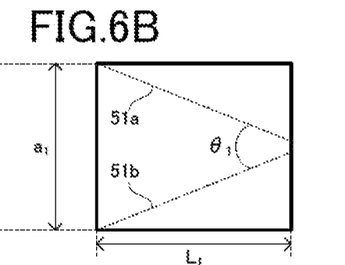
Figure 6C:
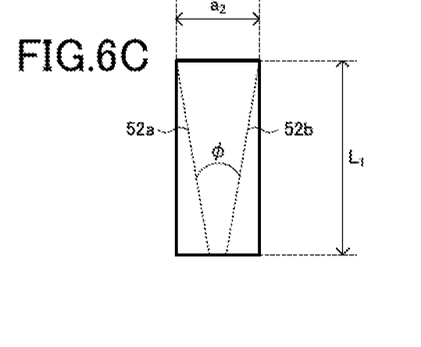
FIG. 6C is a bottom view, illustrating a horn antenna that constitutes the horn antenna array according to the comparative example.

Next, a technical effect of the horn antenna array 1 according to the first example will be explained in comparison with a horn antenna array 50 according to a comparative example (refer to FIG. 5 and FIG. 6). The values of opening sizes $a_1$ and $a_2$, a length $L_1$, and an opening angle $\theta_1$ in FIG. 6 are the same as those in FIG. 2.

In the horn antenna array 50 according to the comparative example, on an electromagnetic wave incident side, ends of an inner upper surface 51a and an inner lower surface 51b of a horn are aligned with ends of inner side surfaces 52a and 52b of the horn. Thus, an angle made by the inner side surfaces 52a and 52b (i.e., an opening angle $\varphi$) is smaller than an angle made by the inner upper surface 51a and the inner lower surface 51b (i.e., the opening angle $\theta_1$).

On an x-y plane, the horn antenna array 1 has a remarkably higher gain of the electromagnetic wave that enters obliquely to the detectors of the horn antennas than the horn antenna array 50. This is because the opening angle $\varphi$ is smaller than the opening angle $\theta_1$ (refer to FIG. 3 and FIG. 4).

The resolution associated with the horn antenna array 1 is equivalent to the resolution associated with the horn antenna array 50. In other words, the horn antenna array 1 can efficiently detect the electromagnetic wave that enters obliquely, while preventing the deterioration in the resolution.

Regarding the gain of the electromagnetic wave that enters perpendicularly to the detectors of the horn antennas, there is little difference between the horn antenna array 1 and the horn antenna array 50. Moreover, on a y-z plane, there is also little difference between the horn antenna array 1 and the horn antenna array 50 regarding the gain of the electromagnetic wave that enters obliquely to the detectors of the horn antennas.

Second Example

A horn antenna array according to a second example of the present invention will be explained mainly with reference to FIG. 7 and FIG. 8. The second example is the same as the aforementioned first example, except that a cylindrical lens is provided. Thus, in the second example, the same explanation as that in the first example will be omitted, and the same part will carry the same reference numerals. Basically, only a different point will be explained mainly with reference to FIG. 7 and FIG. 8.

Figure 7:
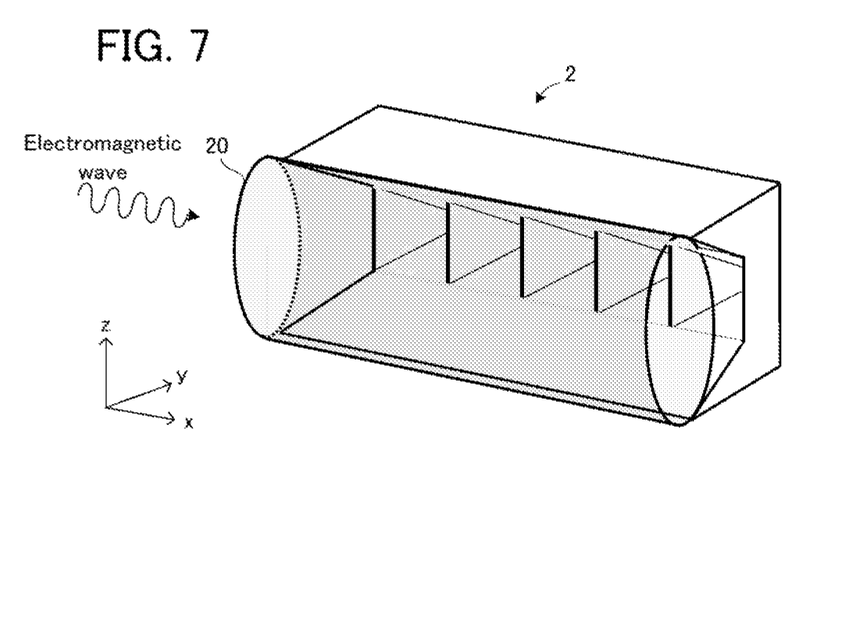
Figure 8A:
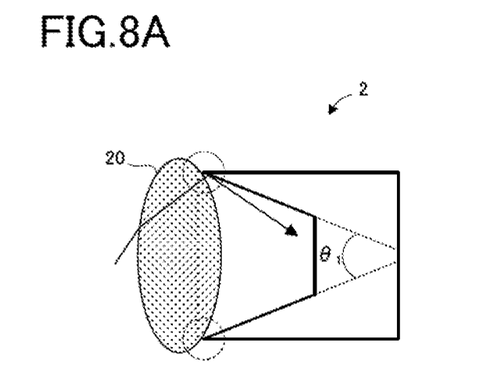
FIG. 8A and FIG. 8B are diagrams illustrating characteristics of the horn antenna array according to the second example.

As illustrated in FIG. 7, a horn antenna array 2 according to the second example is provided with a plurality of horn antennas arranged in an x-axis direction, and a cylindrical lens 20 placed on an electromagnetic wave incident side of the horn antenna array 2. The cylindrical lens 20 is a biconvex cylindrical lens extending in the x-axis direction, as illustrated in FIG. 7.

In the horn antenna array 2, an inner upper surface 11a and an inner lower surface 11b of a horn (refer to FIG. 2) project from ends of an opening of the horn. It is thus possible to bring the cylindrical lens 20 into contact with or close to ends of the inner upper surface 11a and the inner lower surface 11b (refer to dashed circles in FIG. 8(a)).

Figure 8B:
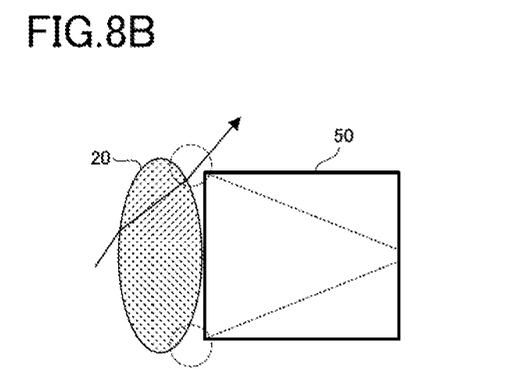

Thus, in particular, on the y-z plane, it is possible to increase an electromagnetic wave that is led to the detectors via the horns and the cylindrical lens 20, out of the electromagnetic wave that enters obliquely to the detectors of the horn antennas, in comparison with the horn antenna array according to the comparative example (refer to FIG. 8(b)).

Moreover, even regarding the electromagnetic wave that enters perpendicularly to the detectors of the horn antennas, it is possible to improve the gain of the electromagnetic wave that enters perpendicularly, because light is converged by the cylindrical lens 20. It is possible to further improve the gain of the electromagnetic wave that enters perpendicularly, particularly by associating a converging angle of the cylindrical lens 20 with the opening angle $\theta_1$.

The present invention is not limited to the aforementioned embodiments and examples, but various changes may be made, if desired, without departing from the essence or spirit of the invention which can be read from the claims and the entire specification. A horn antenna array that involves such changes is also intended to be within the technical scope of the present invention.

DESCRIPTION OF REFERENCE NUMERALS AND LETTERS 1, 2, 50 horn antenna array
11a, 51a inner upper surface
11b, 51b inner lower surface
12a, 12b, 52a, 52b inner side surface
20 cylindrical lens

The invention claimed is:

1. A horn antenna array comprising a plurality of horn antennas arranged in one direction, wherein
each of the plurality of horn antennas includes:
a first side, a second side, a first pair of inclined planes, and second pair of inclined planes, the first and second pairs of inclined planes extending from the first side toward the second side, which define a frustum-shape horn, and
ends of the first pair of inclined planes are arranged in the one direction and extend beyond ends of the second pair of inclined planes.

2. The horn antenna array according to claim 1, wherein an angle made by the first pair of inclined planes arranged in the one direction is equal to an angle made by the second pair of inclined planes.

3. The horn antenna array according to claim 2, wherein the horn antenna array further comprises a biconvex cylindrical lens extending in the one direction, and
the ends of the first pair of inclined planes arranged in the one direction are arranged to be brought into contact with or close to a convex surface of the cylindrical lens.

4. The horn antenna array according to claim 3, wherein an angle made by the pair of inclined planes arranged in the one direction corresponds to a converging angle of the cylindrical lens.

5. The horn antenna array according to claim 1, wherein the horn antenna array further comprises a biconvex cylindrical lens extending in the one direction, and
the ends of the first pair of inclined planes arranged in the one direction are arranged to be brought into contact with or close to a convex surface of the cylindrical lens.

6. The horn antenna array according to claim 5, wherein an angle made by the first pair of inclined planes arranged in the one direction corresponds to a converging angle of the cylindrical lens.

7. The horn antenna array according to claim 1, further comprising a pair of common inclined planes each made up of portions of the first pair of inclined planes of each of the plurality of horn antennas that extend from the ends of the second pair of inclined planes of each of the plurality of horn antennas to the ends of the first pair of inclined planes of the plurality of horn antennas.

* * * * *